(12) United States Patent
Segale et al.

(10) Patent No.: US 10,518,263 B2
(45) Date of Patent: Dec. 31, 2019

(54) CARTRIDGE WITH LAMINATED MANIFOLD

(71) Applicant: Illumina, Inc., San Diego, CA (US)

(72) Inventors: Darren Segale, San Diego, CA (US); Hai Tran, San Diego, CA (US); Paul Crivelli, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 16/264,146

(22) Filed: Jan. 31, 2019

(65) Prior Publication Data

US 2019/0240660 A1    Aug. 8, 2019

Related U.S. Application Data

(60) Provisional application No. 62/626,022, filed on Feb. 3, 2018.

(30) Foreign Application Priority Data

Mar. 19, 2018    (NL) .................................. N2020616

(51) Int. Cl.
*A61J 1/06* (2006.01)
*H01S 4/00* (2006.01)
(Continued)

(52) U.S. Cl.
CPC ..... *B01L 3/502715* (2013.01); *B01J 19/0046* (2013.01); *B01J 2219/0074* (2013.01); *B01L 9/527* (2013.01)

(58) Field of Classification Search
CPC .. A61J 1/06; H01S 4/00; G01N 35/00; G01N 15/06; G01N 33/00; G01N 33/48; B01L 3/5027; B01L 3/5023
(Continued)

(56) References Cited

U.S. PATENT DOCUMENTS 6,653,124 B1 * 11/2003 Freeman ............... B01L 3/5027
435/297.1
6,772,513 B1 * 8/2004 Frye-Mason ..... B01L 3/502715
137/597
(Continued)

FOREIGN PATENT DOCUMENTS

WO    2009/102688    8/2009
WO    2015/183871    12/2015
WO    2017/072513    5/2017

*Primary Examiner* — Brian J. Sines
(74) *Attorney, Agent, or Firm* — Illumina, Inc.

(57) ABSTRACT

A circuit with electrical interconnect for external electronic connection and sensor(s) on a die are combined with a laminated manifold to deliver a liquid reagent over an active surface of the sensor(s). The laminated manifold includes fluidic channel(s), an interface between the die and the fluidic channel(s) being sealed. Also disclosed is a method, the method including assembling a laminated manifold including fluidic channel(s), attaching sensor(s) on a die to a circuit, the circuit including an electrical interconnect, and attaching a planarization layer to the circuit, the planarization layer including a cut out for the die. The method further includes placing sealing adhesive at sides of the die, attaching the laminated manifold to the circuit, and sealing an interface between the die and fluidic channel(s).

20 Claims, 5 Drawing Sheets

(51) Int. Cl.
*G01N 35/00* (2006.01)
*G01N 15/06* (2006.01)
*G01N 33/00* (2006.01)
*G01N 33/48* (2006.01)
*B01L 3/00* (2006.01)
*B01J 19/00* (2006.01)
*B01L 9/00* (2006.01)

(58) Field of Classification Search
USPC .................. 422/68.1, 502, 503, 554; 436/43
See application file for complete search history.

(56) References Cited

U.S. PATENT DOCUMENTS

| | | |
|---|---|---|
| 7,246,524 B1 * | 7/2007 | Kholwadwala ........... B64C 3/46 |
| | | 73/715 |
| 9,404,881 B2 | 8/2016 | Glezer et al. |
| 9,555,631 B2 | 1/2017 | Arthur et al. |
| 2002/0124896 A1 | 9/2002 | O'Connor et al. |
| 2004/0013545 A1 * | 1/2004 | Brown ................. F04B 43/043 |
| | | 417/413.3 |
| 2007/0122314 A1 | 5/2007 | Strand et al. |
| 2008/0004783 A1 | 2/2008 | Strand et al. |
| 2009/0079976 A1 * | 3/2009 | Cunningham ........ B01L 3/5027 |
| | | 356/246 |
| 2012/0210580 A1 * | 8/2012 | Dietl .................... B41J 2/17513 |
| | | 29/890.1 |
| 2013/0044431 A1 | 2/2013 | Koeneman |
| 2013/0320999 A1 | 12/2013 | Deane |
| 2015/0132860 A1 * | 5/2015 | Cook ................. G01N 35/1079 |
| | | 436/501 |
| 2017/0096005 A1 | 4/2017 | Arthur |

* cited by examiner

CARTRIDGE WITH LAMINATED MANIFOLD

CROSS REFERENCE TO RELATED APPLICATIONS

This application claims priority to U.S. Provisional Application No. 62/626,022 filed on Feb. 3, 2018 and Dutch Patent Application No. N2020616 filed on Mar. 19, 2018. The entire contents of each of the aforementioned applications are incorporated herein by reference.

BACKGROUND

Current cartridges for biological or chemical analysis do not handle liquid reagents in an efficient manner. For example, the fluidic path is long, going from the reagent storage area through a conventional manifold to the die, the die including semiconductor sensor(s). The arrangement may slow the analysis and results in large volumes of wash reagent used for each cycle.

Therefore, there is a need for a more efficient fluidic path design.

SUMMARY

The shortcomings of pre-existing approaches may be overcome and additional advantages are provided through the provision, in one aspect, of an apparatus. The apparatus comprises a circuit and at least one sensor on a die coupled to the circuit, the circuit comprising an electrical interconnect for external electrical connection, and a laminated manifold attached to the circuit to deliver a liquid reagent over an active surface of the at least one sensor, the laminated manifold comprising at least one fluidic channel, an interface between the die and the at least one fluidic channel being sealed.

In accordance with yet another aspect, a method is provided. The method comprises assembling a laminated manifold, the laminated manifold comprising at least one fluidic channel, attaching at least one sensor on a die to a circuit, the circuit comprising an electrical interconnect, and attaching a planarization layer to the circuit, the planarization layer comprising a cut out for the die. The method further comprises placing sealing adhesive at sides of the die, attaching the laminated manifold to the circuit, and sealing an interface between the die and the at least one fluidic channel, the laminated manifold and attached circuit together comprise an assembly.

BRIEF DESCRIPTION OF THE DRAWINGS

These, and other objects, features and advantages of this disclosure will become apparent from the following detailed description of the various aspects thereof taken in conjunction with the accompanying drawings, in which:

FIG. 5 is a perspective view of one example of the circuit with the sensor attached thereto, in accordance with one or more aspects of the present disclosure.

FIG. 6 depicts attaching a planarization layer to the circuit of FIG. 5 via, for example, using a bonding layer including a pressure-sensitive adhesive, in accordance with one or more aspects of the present disclosure.

FIG. 7 depicts dispensing and curing a bridge adhesive to the structure of FIG. 6, in accordance with one or more aspects of the present disclosure.

FIG. 8 depicts one example of attaching a laminated manifold (e.g., as described with respect to FIG. 2) to the circuit of FIG. 7 via, for example, a bonding layer (FIG. 2) including a pressure-sensitive adhesive, in accordance with one or more aspects of the present disclosure.

FIG. 9 depicts one example of forming wire bonding to the structure of FIG. 8, encapsulating the wire bonding and attaching a flow cell channel, in accordance with one or more aspects of the present disclosure.

FIG. 10 depicts one example of connecting the structure of FIG. 9 to the reagent rotor and the cartridge body, in accordance with one or more aspects of the present disclosure.

DETAILED DESCRIPTION

Figure 1:
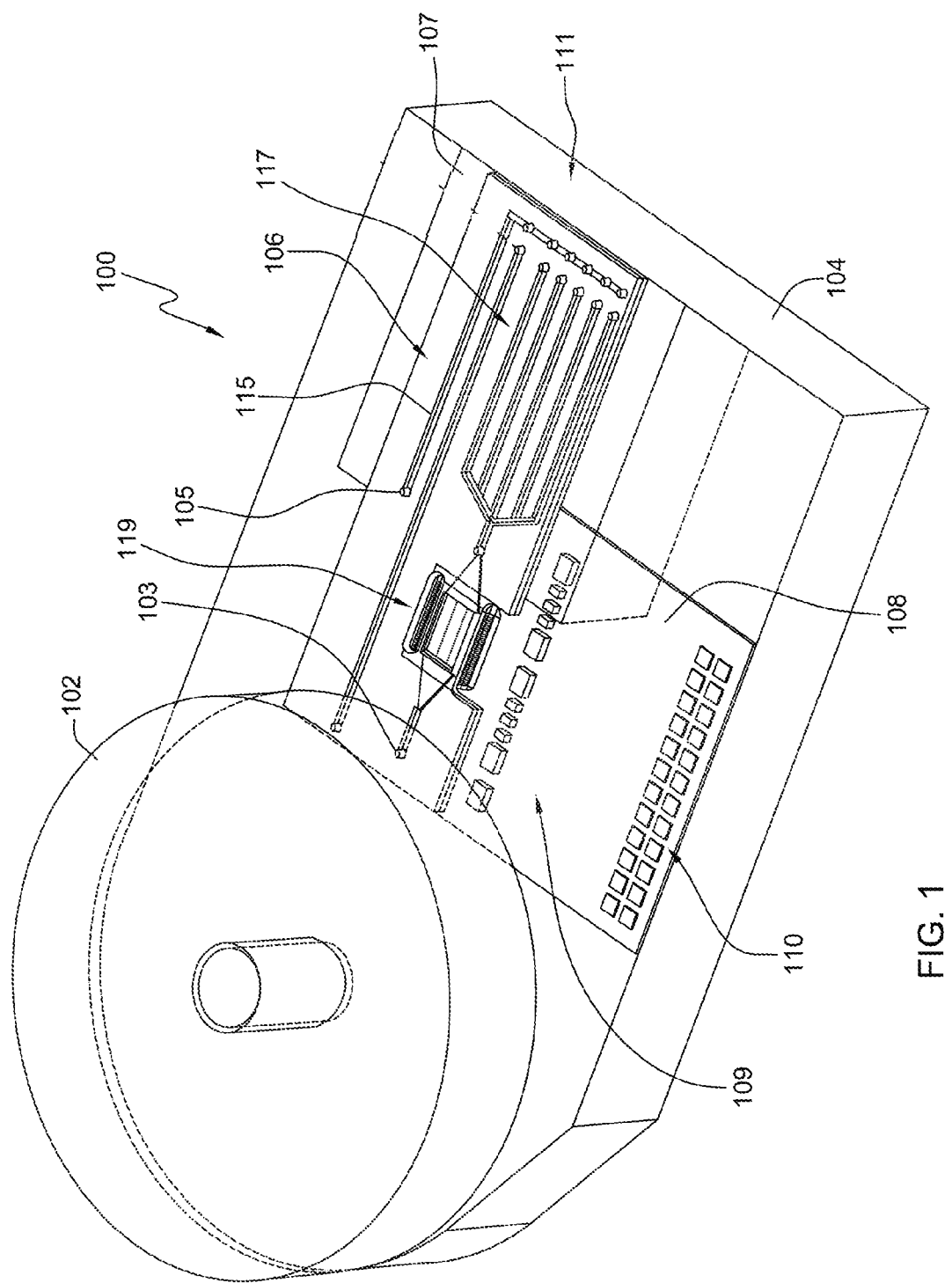
FIG. 1 is a perspective view of one example of a cartridge with a sensor and laminated manifold, useable for, e.g., biological or chemical analysis, in accordance with one or more aspects of the present disclosure.

Aspects of the present disclosure and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the relevant details. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Approximating language, as used herein throughout the specification and claims, may be applied to modify any quantitative representation that may permissibly vary without resulting in a change in the basic function to which it is related. Accordingly, a value modified by a term or terms, such as "about" or "substantially," is not limited to the precise value specified. In some instances, the approximating language may correspond to the precision of an instrument for measuring the value.

The terminology used herein is for the purpose of describing particular examples only and is not intended to be limiting. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises,"

"has," "includes" or "contains" one or more steps or elements possesses those one or more steps or elements, but is not limited to possessing only those one or more steps or elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

As used herein, the term "connected," when used to refer to two physical elements, means a direct connection between the two physical elements. The term "coupled," however, can mean a direct connection or a connection through one or more intermediary elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

As used herein, unless otherwise specified, the approximating terms "about," "substantially" and the like, used with a value, such as measurement, size, etc., means a possible variation of plus or minus ten percent of the value.

As used herein, the terms "bond," "bonded" and "bonding" refer to two things being joined securely together using an adhesive or bonding agent together with a heat process or pressure. As used herein, the term "attach" refers to joining two things together, with or without the use of a fastener (e.g., screw, adhesive or bonding agent, etc.) Thus, the term "bond" is a subset of the term "attach."

Reference is made below to the drawings, which are not drawn to scale for ease of understanding, wherein the same reference numbers are used throughout different figures to designate the same or similar components.

The present disclosure relates to biological or chemical analysis, and more particularly, to a circuit with sensor(s) connected to a laminated manifold for efficient delivery of a liquid reagent to an active surface of the sensor(s).

FIG. 1 is a perspective view of one example of a cartridge 100, which may be used for, e.g., biological or chemical analysis. In one example, the cartridge may be used to enable sequencing, for example, DNA sequencing, e.g., sequencing-by-synthesis or next-generation sequencing (also known as high-throughput sequencing). In another example, the cartridge may be used to enable genotyping. As one skilled in the art will know, genotyping involves determining differences in the genetic make-up (genotype) of an individual by examining the individual's DNA sequence using biological assays and comparing it to another individual's sequence or a reference sequence. The cartridge, which may be consumable or reusable, includes a reagent rotor 102, a cartridge body 104 (with pump 107 internal to cartridge body), a laminated manifold 106 for delivering the reagent and a circuit 108 with passive electronics 109 for various functions of the cartridge and electrical interconnect 110 for external electrical connection. The laminated manifold is used to deliver a liquid reagent to an active surface of a sensor (134, FIG. 2), in accordance with one or more aspects of the present disclosure. Although the pump in this example is internal to the cartridge, it will be understood that the pump may instead be on a surface of the cartridge or external to the cartridge.

The fluid flow of the reagent from storage (rotor 102 in this example) is active via pump 107. The pump draws the liquid reagent from the rotor, through the laminated manifold 106 and to flow cell 119 over the active surface (138, FIG. 3) of the sensor (134, FIG. 2) through fluidic opening 103. The liquid reagent exits the flow cell to the arms of what looks like a candelabra (channels 117). The liquid reagent returns to the pump through the array of pinch valves 111 located, for example, at the bottom of the cartridge. The pinch valves may normally be closed, such that which pinch valve is open when the pump aspirates determines which arm of the candelabra is used for the return. Any excess fluid from channels 117 return to the pump through fluidic path 115 and fluidic opening 105. The microfluidic pump maintains a flow of reagent(s) through the cartridge for sensing. In one example, the pump takes the form of a self-priming micro-pump.

Non-limiting examples of the function(s) of the sensor include, for example, light sensing (e.g., having a predetermined range of wavelengths sensed), detecting the presence of one or more substances (e.g., biological or chemical substance) and detecting a change in concentration of something (e.g., ion concentration). The sensor may be, for example, semiconductor-based (e.g., an integrated circuit), the individual devices of which may be planar or non-planar (e.g., Fin Field Effect Transistor (FinFET) based). In one example, the sensor may be a CMOS (Complementary Metal-Oxide Semiconductor) image sensor. As one skilled in the art will know, the circuitry of a CMOS image sensor includes passive electronic elements, such as a clock and timing generation circuit, an analog-to-digital converter, etc., as well as an array of photodetectors to convert photons (light) to electrons, which is then converted to a voltage. In another example, the sensor may be a CCD (Charge Coupled Device), another type of image sensor.

As one skilled in the art will understand, "CMOS" refers to a technology used to fabricate integrated circuits. As used herein, "CMOS sensor" and "CMOS image sensor" refer to sensors fabricated using CMOS technology. The "complementary" aspect of the name refers to the inclusion of both n-type and p-type metal-oxide semiconductor field effect transistors (MOSFETs) in integrated circuits (ICs) fabricated using CMOS technology. Each MOSFET has a metal gate with a gate dielectric, such as an oxide (hence, the "Metal-Oxide" part of the name) and a semiconductor material below the gate (corresponds to "Semiconductor" in the name). ICs are fabricated on a die, which is a portion of a semiconductor substrate or wafer that is cut out after fabrication, and ICs fabricated using CMOS technology are characterized by, for example, high noise immunity and low static power consumption (one of the transistors is always off).

In one example, a CMOS image sensor may include, for example, millions of photodetectors, also called pixels. Each pixel includes a photosensor, which accumulates charge from the light, an amplifier to convert the accumulated charge into a voltage, and a pixel-select switch. Each pixel may also include, for example, an individual microlens to capture more of the light, or have other enhancements to improve the image such as, for example, noise reduction.

One example of the fabrication of a semiconductor device fabricated using CMOS technology will now be provided.

Starting, for example, with a p-type semiconductor substrate, the NMOS region may be protected while an n-type well is created in the PMOS region. This may be accomplished using, for example, one or more lithographic processes. A thin gate oxide and gate (e.g., polysilicon) may then be formed in both the NMOS and PMOS regions. N+ type dopant regions may be formed in the p-type substrate of the NMOS region on either side of the dummy gate (i.e., the source and drain are formed), and one region of the n+ type dopant as the body (here, the well) contact in the PMOS region. This may be accomplished using, for example, a mask. The same process of masking and doping may then be used to form the source and drain in the PMOS region and the body contact in the NMOS region. Metallization to form the terminals to the various regions of the NMOS and PMOS transistors (i.e., body, source, drain and gate) may then be performed. Unlike CCDs, CMOS image sensors may include other circuits on the same chip at little to no extra cost, providing functions such as image stabilization and image compression on-chip.

Figure 2:
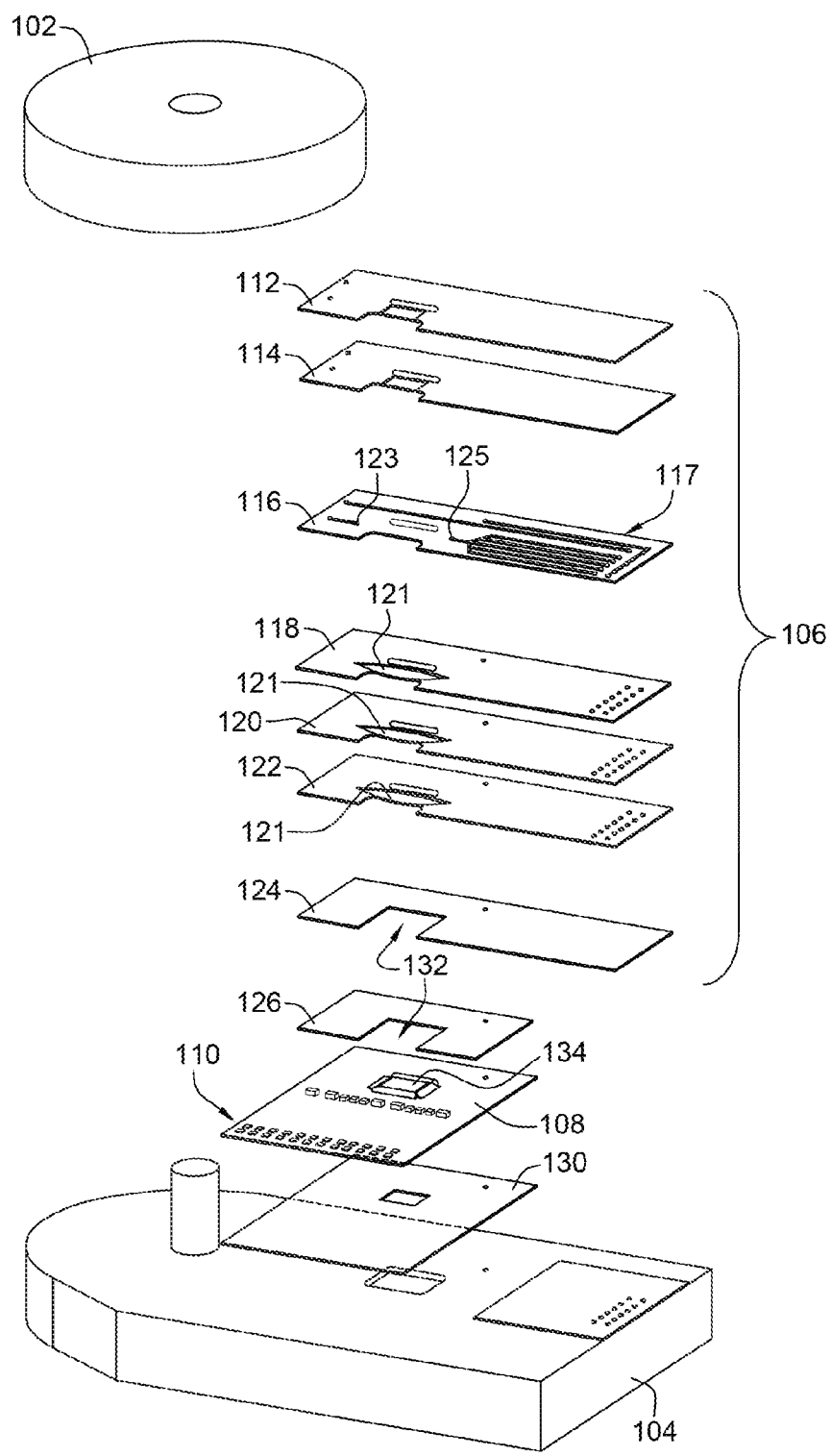
FIG. 2 is a blown-up view of one example of the laminated manifold of FIG. 1, showing the various layers of the laminated manifold, in accordance with one or more aspects of the present disclosure.

FIG. 2 is an exploded view of one example of the laminated manifold 106 of FIG. 1. The laminate includes a lidding layer 112, which may be, for example, a polymer film (e.g., polyethylene terephthalate (PET) or poly(methyl methacrylate (PMMA)), and may have a thickness of, e.g., about 100 microns to about 700 microns in one example, and about 100 microns to about 400 microns in another example. The laminated manifold also includes a fluidic distribution layer 116 for distributing the liquid reagent(s), which may have a thickness of, for example, about 200 microns to about 1000 microns in one example, and about 300 microns to about 700 microns in another example. Fluidic distribution layer 116 may be, for example, a material with low or no autofluorescence, e.g., a thin plastic film or glass. Non-limiting examples of materials for layer 116 include: PMMA, commercially available from, for example, Evonit Corporation, Parsippany, N.J.; a Cobalt Phosphide (CoP) film, commercially available from, for example, American Elements, Los Angeles, Calif.; a Cyclic Olefin Copolymer (COC), commercially available from, for example, Zeon Chemicals L.P., Louisville, Ky.; and borosilicate glass, commercially available from, for example, Schott North America, Inc., Elmsford, N.Y. A fluidic path through channels 117 for bulk or relatively thick fluid is defined by layer 116. The channels are sized to enable fluid flow with low impedance, for example, having a width of between about 0.25 mm and about 1 mm. Between the lidding and fluidic distribution layers is an adhesive layer 114, which may have a thickness of, for example, about 20 microns to about 50 microns in one example, and about 25 microns in another example. In one example, the adhesive layer may include a pressure-sensitive adhesive for securely attaching under pressure the layers directly above and below the pressure-sensitive adhesive. Non-limiting examples of the adhesive of layer 114 include an acrylic or silicone adhesive. The pressure-sensitive adhesive may be part of, for example, a single-sided adhesive tape that may include, for example, a rigid plastic liner (e.g., PET) with the adhesive thereon. Such adhesive tapes are commercially available from, for example, 3M in St. Paul, Minn., or Adhesives Research, Inc. in Glen Rock, Pa. As one skilled in the art will know, a pressure-sensitive adhesive, when under pressure, creates a bond without the need for solvent, water or heat.

The laminated manifold of FIG. 2 further includes a substrate layer 120, and the substrate layer may include an aperture 121, along with layers 118 and 122, which overlap openings 123 and 125 in layer 116, allowing reagent(s) to reach the active surface (138, FIG. 3) of the sensor from the channels in layer 116. In one example, the openings are sized similar to the channels. The substrate layer may have a thickness of, for example, about 50 microns to about 70 microns in one example, and about 60 microns in another example. Substrate layer 120 may be, for example, a polymer film (e.g., PET or PMMA). The fluid flow over the sensor transitions from the relatively thick flow in the channels of the fluidic distribution layer to a relatively thin fluid flow, which provides an efficient use of the fluid. The fluidic path over the sensor is shown through flow line 156 in FIG. 4. In one example, a chemical reaction of only the fluid passing over the sensor, for example, fluorescence, may be observable to a user. Between the fluidic distribution layer and the substrate layer is an adhesive layer 118, which may have a thickness of, for example, about 20 microns to about 50 microns in one example, and about 25 microns in another example. In one example, layer 118 may include a pressure-sensitive adhesive for securely attaching under pressure the layers directly above and below the pressure-sensitive adhesive. Non-limiting examples of the adhesive of layer 118 include an acrylic or silicone adhesive. The pressure-sensitive adhesive may be part of, for example, a double-sided adhesive tape that may include, for example, a rigid plastic liner (e.g., PET) with the adhesive thereon. Such adhesive tapes are commercially available as described above. The structure further includes a planarization layer 124 to provide support to the laminated manifold and to present an even surface to the circuit 108, which may have a thickness of, for example, about 500 microns to about 700 microns in one example, and about 600 microns in another example, in accordance with one or more aspects of the present disclosure. In one example, the planarization layer is about the same thickness as the die. In one example, the material of the planarization layer 124 may include extruded plastic, for example, PET, polypropylene or polycarbonate. Between substrate layer 120 and planarization layer 124 is an adhesive layer 122, which may have a thickness of, for example, about 20 microns to about 50 microns in one example, and about 25 microns in another example. In one example, layer 122 may include a pressure-sensitive adhesive for securely attaching under pressure the layers directly above and below the pressure-sensitive adhesive. Non-limiting examples of the adhesive of layer 122 include an acrylic or silicone adhesive. The pressure-sensitive adhesive may be part of, for example, a double-sided adhesive tape that may include, for example, a rigid plastic liner (e.g., PET) with the adhesive thereon. Such adhesive tapes are commercially available as described above.

The laminated manifold 106 may be bonded to circuit 108, for example, via bonding layer 126, which may include, for example, a pressure-sensitive adhesive with a thickness of, e.g., about 50 microns to about 70 microns in one example, and about 60 microns in another example. Non-limiting examples of the adhesive of layer 126 include an acrylic or silicone adhesive. The pressure-sensitive adhesive may be part of, for example, a single-sided adhesive tape that may include, for example, a rigid plastic liner (e.g., PET) with the adhesive thereon. Such adhesive tapes are commercially available as described above. The circuit may be flexible or rigid (e.g., PCB board) and have a thickness of, for example, about 200 microns to about 300 microns in one example, and about 250 microns in another example.

Both the planarization layer 124 and bonding layer 126 include a cut-out 132 for a sensor 134 on the circuit such that the active surface (138, FIG. 3) may be substantially planar with the laminated manifold when the reagent is in contact with the active surface. Finally, the circuit is bonded to the cartridge body 104 via bonding layer 130, which may include a pressure-sensitive adhesive and may have a thickness of, for example, about 50 microns to about 150 microns in one example, and about 100 microns in another example. Non-limiting examples of the adhesive of layer 130 include an acrylic or silicone adhesive. The pressure-sensitive adhesive may be part of, for example, a double-sided adhesive tape that may include, for example, a rigid plastic liner (e.g., PET) with the adhesive thereon. Such adhesive tapes are commercially available as described above.

Figure 3:
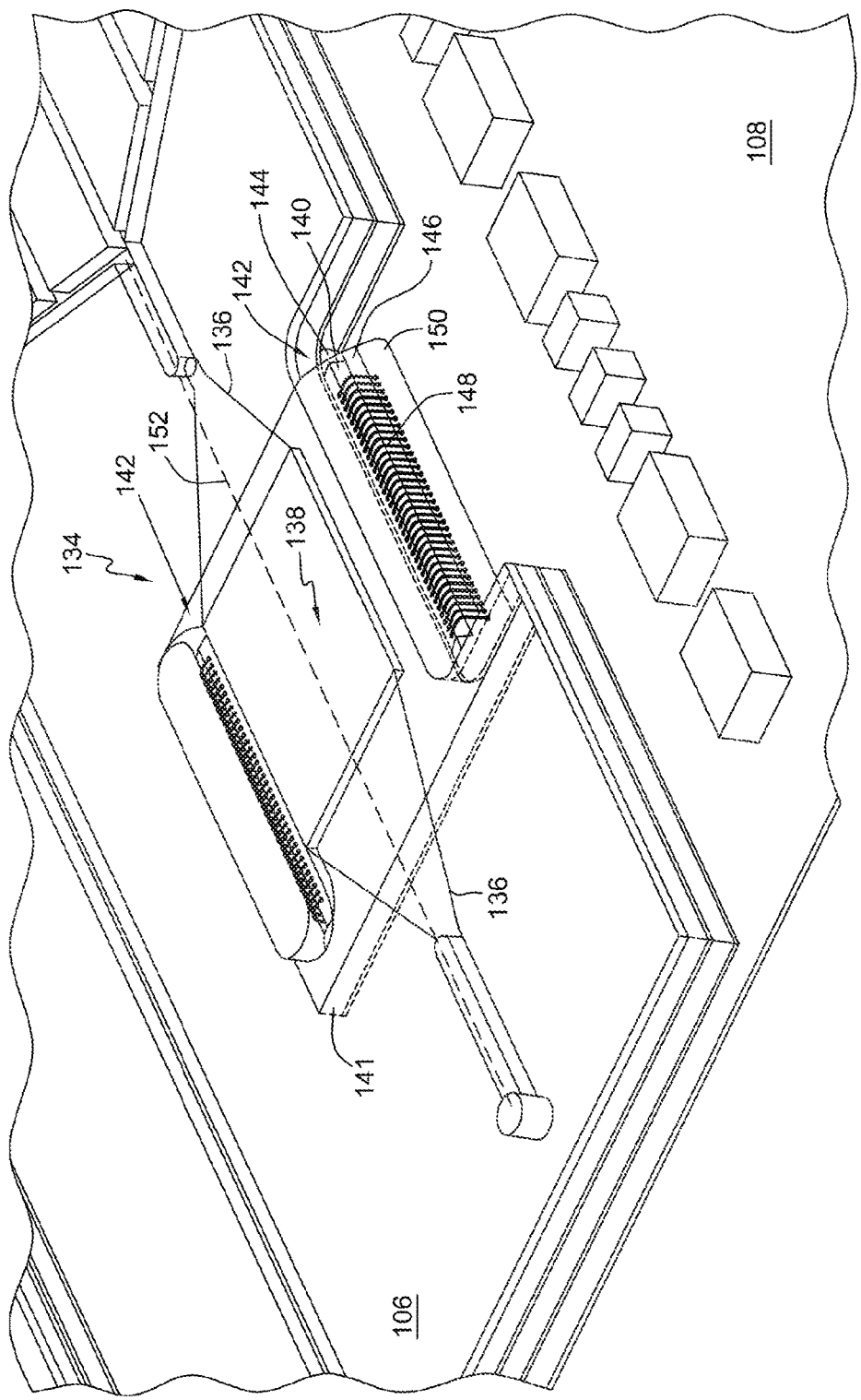
FIG. 3 is a perspective view of one example of the sensor in relation to the laminated manifold and the circuit, in accordance with one or more aspects of the present disclosure.

FIG. 3 is a perspective view of one example of sensor 134 in relation to the laminated manifold 106 and circuit 108. The active surface of the sensor and the laminated manifold structure surrounding and above the sensor (i.e., fluidic distribution layer 116, FIG. 2) where the reagent(s) are introduced, constitutes a flow cell. A flow cell channel 136 delivers liquid reagent(s) to an active surface 138 of the sensor(s), situated on die 140, and then carries the liquid reagent(s) away from the sensor. Substance(s), for example, biological or chemical substances(s), may be introduced into the space for on-chip sensing by the active surface of the sensor. Where semiconductor based, the sensor may be fabricated on a silicon substrate (e.g., a silicon wafer), which becomes the die when cut from the silicon wafer. The thickness of the die depends on the size (diameter) of the silicon wafer. For example, a standard silicon wafer with a 51 mm diameter may have a thickness of about 275 microns, while a standard silicon wafer with a diameter of 300 mm may have a thickness of about 775 microns. As used herein, the active area of the sensor(s) refers to the sensor surface that will come into contact with the reagent(s) for sensing. There may be more than one sensor on the die, and different sensors may be included on the same die. The flow cell channel may include, for example, silicate glass (e.g., aluminosilicate glass). The die is sealed at sealing areas 142. In one example, each sealing area includes, for example, a bridge adhesive 144, structural adhesive 146 and wire bonding 148 using, for example, gold wire, which is covered by a wire bond encapsulate 150, in accordance with one or more aspects of the present disclosure. The die may be attached to circuit 108 by an adhesive, for example, a dispersed ultraviolet-curable adhesive or a pressure-sensitive adhesive tape (e.g., acrylic or silicon adhesive). Electrical connection between the circuit and the sensor may be accomplished a number of ways, for example, low-temperature wire bonding, which prevents exposure of the die to high temperatures. The wire bonds are relatively small and may be ultrasonically welded wires that make electrical connections between the sensor and the circuit. These electrical connections may be protected with, for example, an adhesive dispersed on the wires (e.g., an ultraviolet (UV)-curable adhesive), which completely encapsulates the wires when cured with UV light, transforming into a solid form. A commercially available UV-curable adhesive may be obtained from, for example, Dymax Corporation, Torrington, Conn. The interface 141 between the die 140 and the manifold's fluidic channel is sealed so that the active surface of the sensor comes into contact with the fluid(s) in the laminated manifold, while also isolating the liquid from electrical interconnects and other aspects of the circuit that may be shorted out by the presence of electrically conductive liquid.

Figure 4:
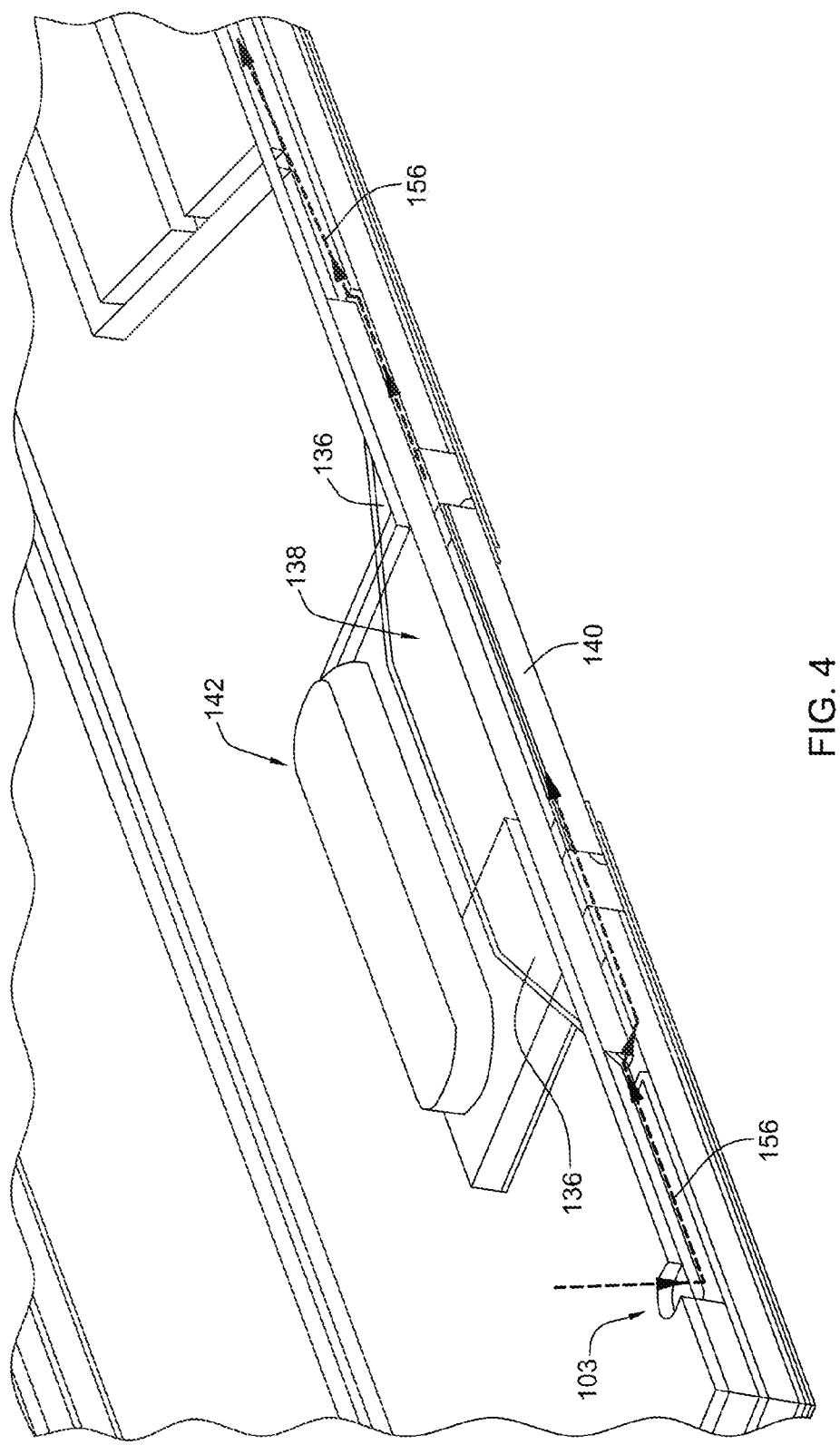
FIG. 4 is a perspective view of one example of a cross-section of the sensor area taken across a line of FIG. 3, in accordance with one or more aspects of the present disclosure.

FIG. 4 is a perspective view of one example of a cross-section of the sensor area taken across line 152 of FIG. 3. As shown, an inlet 103 from a reagent reservoir (e.g., within reagent rotor 102 shown in FIG. 1) distributes the reagent via force of the pump (107, FIG. 1) to a flow line 156 connected to flow cell channel 136 over active surface 138 of the sensor, in accordance with one or more aspects of the present disclosure.

Figure 5:
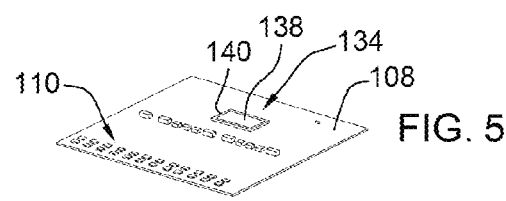
FIGS. 5-10 depict various stages of constructing the cartridge of FIG. 1.

FIGS. 5-10 depict various stages of constructing the cartridge 100 of FIG. 1. FIG. 5 is a perspective view of one example of circuit 108 with sensor 134 attached thereto, for example, bonded together, in accordance with one or more aspects of the present disclosure.

Figure 6:
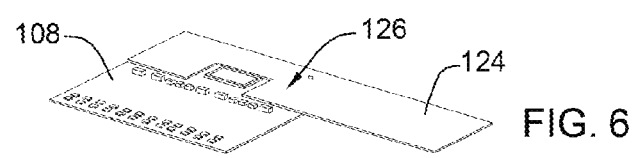

FIG. 6 depicts attaching planarization layer 124 to the circuit 108 of FIG. 5 by, for example, using a bonding layer 126, in accordance with one or more aspects of the present disclosure.

Figure 7:
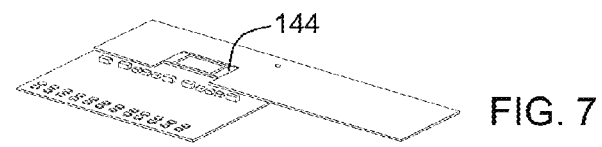

FIG. 7 depicts dispensing and curing bridge adhesive 144 to the structure of FIG. 6, in accordance with one or more aspects of the present disclosure.

Figure 8:
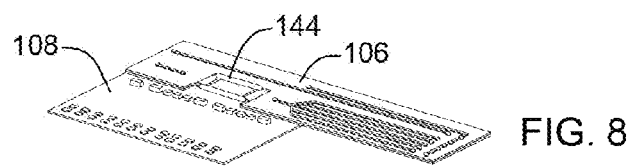

FIG. 8 depicts one example of attaching a laminated manifold 106 (e.g., as described with respect to FIG. 2) to the planarization layer 124 on circuit 108 of FIG. 7 via, for example, using bonding layer 122 (FIG. 2), in accordance with one or more aspects of the present disclosure.

Figure 9:
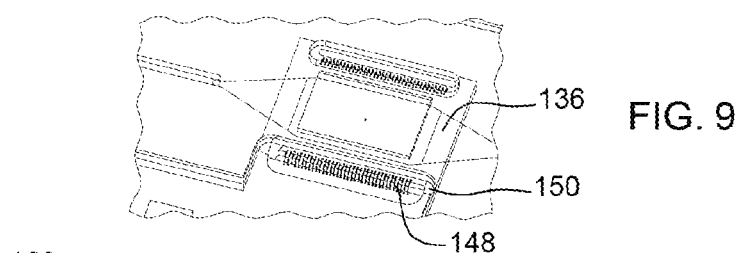

FIG. 9 depicts one example of wire bonding 148 the structure of FIG. 8, for example, low-temperature wire bonding, encapsulating the wire bonding via, for example, wire bond encapsulant 150 and attaching flow cell channel 136, a V-shaped extension of the fluidic pathway on opposite sides of the sensor delivering the reagent(s) to the active surface of the sensor for sensing, in accordance with one or more aspects of the present disclosure. The wire bond may include a metal, for example, aluminum, copper, silver or gold.

Figure 10:
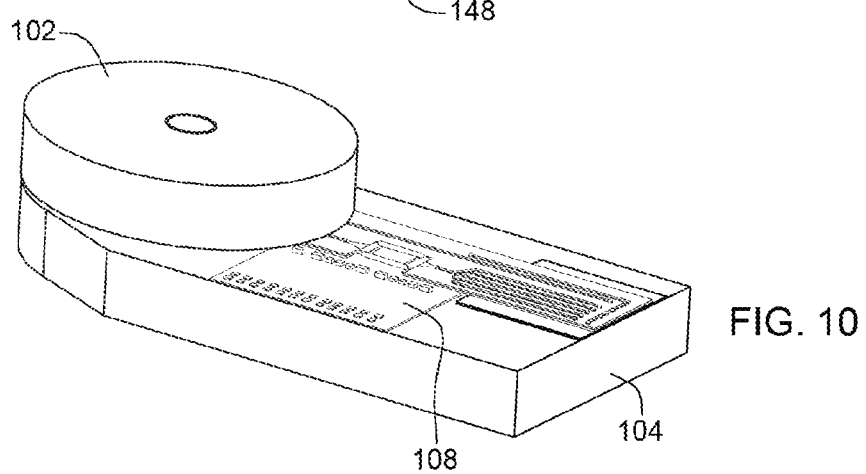

FIG. 10 depicts one example of attaching the structure of FIG. 9 to the reagent rotor 102 and cartridge body 104, for example, by bonding using bonding layer 130 (FIG. 2), which may include an adhesive (e.g., a pressure-sensitive adhesive as previously described), in accordance with one or more aspects of the present disclosure.

In a first aspect, disclosed above is an apparatus. The apparatus includes a circuit and sensor(s) on a die attached to the circuit, the circuit including an electrical interconnect for external electrical connection, and a laminated manifold attached to the circuit to deliver a liquid reagent over an active surface of the sensor(s), the laminated manifold including fluidic channel(s), an interface between the die and the fluidic channel(s) being sealed.

In one example, the sensor(s) may include, for example, a semiconductor. In another example, the sensor(s) may take the form of, for example, a Complementary Metal-Oxide Semiconductor (CMOS) sensor (e.g., a CMOS image sensor).

In one example, the laminated manifold in the apparatus of the first aspect may include, for example, multiple layers that may include, for example, a top lidding layer, a fluidic distribution layer, a substrate layer, and a bottom planarization layer. In one example, the circuit may be, for example, bonded to the planarization layer, and the planarization layer may have, for example, a thickness that is about a collective thickness of the sensor(s) and die.

In one example, a pressure-sensitive adhesive may be, for example, between adjacent layers of the multiple layers of the laminated manifold.

In one example, adjacent layers of the laminated manifold may be, for example, mechanically connected, for example, via fasteners or screws.

In one example, the apparatus of the first aspect may be, for example, part of a cartridge, such as that used for biological analysis.

In one example, the apparatus of the first aspect may be, for example, part of a cartridge, such as that used for chemical analysis.

In one example, the apparatus of the first aspect may be, for example, part of a cartridge, and the cartridge may further include, for example, a reagent storage and delivery system coupled to the laminated manifold, and a cartridge body and a reagent pump coupled to the reagent storage and delivery system.

In one example, the laminated manifold in the apparatus of the first aspect may have, for example, cut-out(s) for the die. In one example, the die may be, for example, wire bonded to the circuit.

In one example, the apparatus of the first aspect, when in use, a reagent may be, for example, delivered via the laminated manifold over an active surface of the sensor(s). In one example, only the active surface(s) of the sensor(s) is (are) exposed to the reagent.

In a second aspect, disclosed above is a method. The method includes assembling a laminated manifold, the laminated manifold including fluidic channel(s), attaching a die with sensor(s) to a circuit, the circuit including an electrical interconnect. The method further includes attaching a planarization layer to the circuit, the planarization layer including a cut out for the die, placing sealing adhesive at sides of the die, attaching the laminated manifold to the circuit, and sealing an interface between the die and the fluidic channel(s), the laminated manifold and attached circuit together being an assembly.

In one example, the method may further include, for example, attaching the assembly to a cartridge.

In one example, assembling the laminated manifold in the method of the second aspect may include, for example, laminating layers, and the layers may include, for example, a top lidding layer, a fluidic distribution layer, a substrate layer, and a bottom planarization layer. In one example, the laminating may include, for example, using an adhesive between adjacent layers (e.g., a pressure-sensitive adhesive).

In one example, the method of the second aspect may further include, for example, using the assembly for sequencing.

In one example, the method of the second aspect may further include, for example, using the assembly for genotyping.

While several aspects of the present disclosure have been described and depicted herein, alternative aspects may be effected by those skilled in the art to accomplish the same objectives. Accordingly, it is intended by the appended claims to cover all such alternative aspects.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The invention claimed is:

1. Apparatus, comprising:
   a circuit and at least one sensor on a die attached to the circuit, the circuit comprising an electrical interconnect for external electrical connection; and
   a laminated manifold attached to the circuit to deliver a liquid reagent over an active surface of the at least one sensor, the laminated manifold comprising at least one fluidic channel, wherein an interface between the die and the at least one fluidic channel is sealed.

2. The apparatus of claim 1, wherein the at least one sensor comprises a semiconductor.

3. The apparatus of claim 2, wherein the at least one sensor comprises a Complementary Metal-Oxide Semiconductor (CMOS) sensor.

4. The apparatus of claim 1, wherein the laminated manifold comprises a plurality of layers, the plurality of layers comprising:
   a top lidding layer;
   a fluidic distribution layer;
   a substrate layer; and
   a bottom planarization layer.

5. The apparatus of claim 4, wherein the circuit is bonded to the planarization layer, and wherein the planarization layer has a thickness that is about a collective thickness of the at least one sensor and die.

6. The apparatus of claim 4, wherein between adjacent layers of the plurality of layers is a pressure-sensitive adhesive.

7. The apparatus of claim 4, wherein adjacent layers of the plurality of layers are mechanically connected.

8. The apparatus of claim 1, wherein the apparatus is part of a cartridge for biological analysis.

9. The apparatus of claim 1, wherein the apparatus is part of a cartridge for chemical analysis.

10. The apparatus of claim 1, wherein the apparatus is part of a cartridge, and wherein the cartridge further comprises:
    a reagent storage and delivery system coupled to the laminated manifold; and
    a cartridge body and a reagent pump coupled to the reagent storage and delivery system.

11. The apparatus of claim 1, wherein the laminated manifold has at least one cut-out for the die.

12. The apparatus of claim 11, wherein the die is wire bonded to the circuit.

13. The apparatus of claim 1, wherein when in use, a reagent is delivered via the laminated manifold over an active surface of the at least one sensor.

14. The apparatus of claim 13, wherein only the active surface of the at least one sensor is exposed to the reagent.

15. A method, comprising:
    assembling a laminated manifold, the laminated manifold comprising at least one fluidic channel;
    attaching at least one sensor on a die to a circuit, the circuit comprising an electrical interconnect;
    attaching a planarization layer to the circuit, the planarization layer comprising a cut out for the die;
    placing sealing adhesive at sides of the die;
    attaching the laminated manifold to the circuit; and
    sealing an interface between the die and the at least one fluidic channel;
    wherein the laminated manifold and attached circuit together comprise an assembly.

16. The method of claim 15, further comprising attaching the assembly to a cartridge.

17. The method of claim 15, wherein assembling the laminated manifold comprises laminating a plurality of layers, the plurality of layers comprising:
    a top lidding layer;
    a fluidic distribution layer;
    a substrate layer; and
    a bottom planarization layer.

18. The method of claim 17, wherein the laminating comprises using a pressure-sensitive adhesive between adjacent layers of the plurality of layers.

19. The method of claim 15, further comprising using the assembly for sequencing.

20. The method of claim 15, further comprising using the assembly for genotyping.

\* \* \* \* \*